(12) United States Patent
Gardner et al.

(10) Patent No.: US 6,923,781 B2
(45) Date of Patent: Aug. 2, 2005

(54) MASTER BRACE

(76) Inventors: Jermaine W. Gardner, 124 Debbie La., Summerville, SC (US) 29483; Zarah Michelle Gardner, 124 Debbie La., Summerville, SC (US) 29483

( * ) Notice: Subject to any disclaimer, the term of this patent is extended or adjusted under 35 U.S.C. 154(b) by 259 days.

(21) Appl. No.: 10/435,798

(22) Filed: May 12, 2003

(65) Prior Publication Data

US 2004/0015113 A1 Jan. 22, 2004

Related U.S. Application Data

(63) Continuation-in-part of application No. 10/199,258, filed on Jul. 22, 2002, now abandoned.

(51) Int. Cl.$^7$ .................................................. A61F 5/00
(52) U.S. Cl. .......................... 602/27; 602/23; 602/65; 128/882
(58) Field of Search .............................. 602/27, 28, 29, 602/23, 61, 62, 65, 66, 78; 128/882, 869, 845; 2/22; 623/27, 28, 29, 47

(56) References Cited

U.S. PATENT DOCUMENTS

| 4,621,648 | A | * | 11/1986 | Ivany | 602/27 |
|---|---|---|---|---|---|
| 4,630,600 | A | * | 12/1986 | Spencer et al. | 602/27 |
| 5,016,623 | A | * | 5/1991 | Krahenbuhl | 602/27 |
| 5,067,486 | A | * | 11/1991 | Hely | 602/27 |
| 5,092,319 | A | * | 3/1992 | Grim | 602/27 |
| 5,464,384 | A | * | 11/1995 | Cromartie | 602/27 |
| 5,657,767 | A | * | 8/1997 | Nelson et al. | 128/882 |
| 5,676,642 | A | * | 10/1997 | Peters | 602/27 |
| 5,792,087 | A | * | 8/1998 | Pringle | 602/27 |
| 6,022,332 | A | * | 2/2000 | Nelson | 602/27 |
| 6,056,713 | A | * | 5/2000 | Hayashi | 602/27 |
| 6,126,626 | A | * | 10/2000 | Duback et al. | 602/27 |

* cited by examiner

Primary Examiner—Fadi H. Dahbour

(57) ABSTRACT

A brace for supporting the ankle or foot of a wearer includes:
(a) at least two layers, an inner one of the at least two layers being included of an elasticized, close-fitting material, an outer portion of the layers being included of a supportive, yet flexible, protective material; and
(b) at least four splints attached to the outer layer portion, with a first, generally L-shaped one of the at least four splints having its longitudinal axis over the wearer's fibula, the first, fibula splint extending along an outside side of the brace; a second, generally L-shaped splint having a longitudinal axis leg portion over the wearer's tibia, the second, tibia splint extending along an inside side of the brace, the inside side of the brace being opposite the outside side of the brace; a third, Achilles tendon splint extending in a generally vertical direction at a rear of the brace over the wearer's Achilles tendon, the rear of the brace being between the inside side and the outside side of the brace; and a fourth, fifth metatarsal splint extending from the Achilles tendon splint in a generally horizontal direction along an outside of the brace. The brace preferably includes three additional splints.

17 Claims, 9 Drawing Sheets

MASTER BRACE

CROSS REFERENCE TO RELATED DOCUMENT

This invention is a continuation-in-part of U.S. patent application Ser. No. 10/199,258, which was filed in the U.S. Patent & Trademark Office on Jul. 22, 2002 now abandoned.

BACKGROUND OF THE INVENTION

1. Technical Field

The present invention relates to orthopedic ankle and foot braces and supports generally, and more particularly to a foot and ankle brace for protecting a wearer's foot, ankle, and Achilles tendon before or after injury during sports or just daily activities.

2. Background Information

A sprained ankle is an injury where the smaller stabilizing muscles, such as the peroneus longus, tibulis posterior the flexors, extensors, the everters and the inverters, will all need to be rehabilitated. Recovery from such an injury takes approximately six (6) to eight (8) weeks. During that time, the ankle should be properly supported in order to regain flexibility of the muscles.

The ankle and foot brace of the present invention stabilizes and protects the foot and ankle, so as to allow an individual wearer with an ankle or foot injury to walk, run, and jump with confidence during the process of recovery. The brace of the present invention has particular application as an athletic support and rehabilitation device for protecting the foot, ankle, and Achilles tendon from injuries that could cause extensive damage. It can also apply relatively even compression to a swollen ankle.

Some sports participants or laymen who have previously sprained an ankle or injured their foot, or who have fallen arches, hammer toes, tendonitis, etc. desire extra protection, even where no existing injury has been diagnosed. The brace of the present invention protects and supports before and after an injury.

BRIEF SUMMARY OF THE INVENTION

The present invention includes a brace for supporting the ankle or foot of a wearer, including:
(a) at least two layers, an inner one of the at least two layers being comprised of an elasticized, close-fitting material, an outer portion of the layers being comprised of a supportive, yet flexible, protective material; and
(b) at least four splints, each attached to the outer layer portion, with a first, generally L-shaped one of the at least four splints having a longitudinal axis leg portion over the wearer's fibula, the first, fibula splint extending along an outside side of the brace; a second, generally L-shaped splint having a longitudinal axis leg portion over the wearer's tibia, the second, tibia splint extending along an inside side of the brace, the inside side of the brace being opposite the outside side of the brace; a third, Achilles tendon splint extending in a generally vertical direction at a rear of the brace over the wearer's Achilles tendon, the rear of the brace being between the inside side and the outside side of the brace; and a fourth, fifth metatarsal splint extending from the Achilles tendon splint in a generally horizontal direction along an outside of the brace. The brace preferably includes three additional splints: a fifth, arch support splint, a sixth, medial malleolus splint, and/or a seventh, lateral malleolus splint.

The brace of the present invention was created to protect, comfort and rehabilitate the ankle area. The brace is designed to stabilize a weak or injured ankle and protect it, providing individual adequate support while the user is participating in any physical activity. The brace offers support, flexibility and comfort with an advanced level of protection in comparison with existing braces. The appealing features of the present brace include its distinctive design, ease of use, comfort, ease of application, and its high potential to minimize injuries. The brace of the present invention includes seven splints that will stabilize and protect areas of the ankle that are being poorly supported by a number of existing braces or supports. The seven splints that make up the brace are as described herein: Achilles tendon, fifth metatarsal, lateral and medial malleolus, two (2) L-shaped splints that parallel the tibia-fibular region, and an arch support splint. With the security and protection of the seven splints, the brace is designed to prevent inversion and eversion of the ankle. The brace offers solid protection throughout the invention, imposing confidence upon the wearer of the brace. The brace is an all in one stabilizing and supportive brace constructed to fit the right or left foot for better support and protection. The sizes for men and women will vary, considering a slight difference in structure. To provide the appropriate support to either gender, it is preferred that the brace be constructed in different sizes.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein.

DETAILED DESCRIPTION OF THE INVENTION

Figure 1:
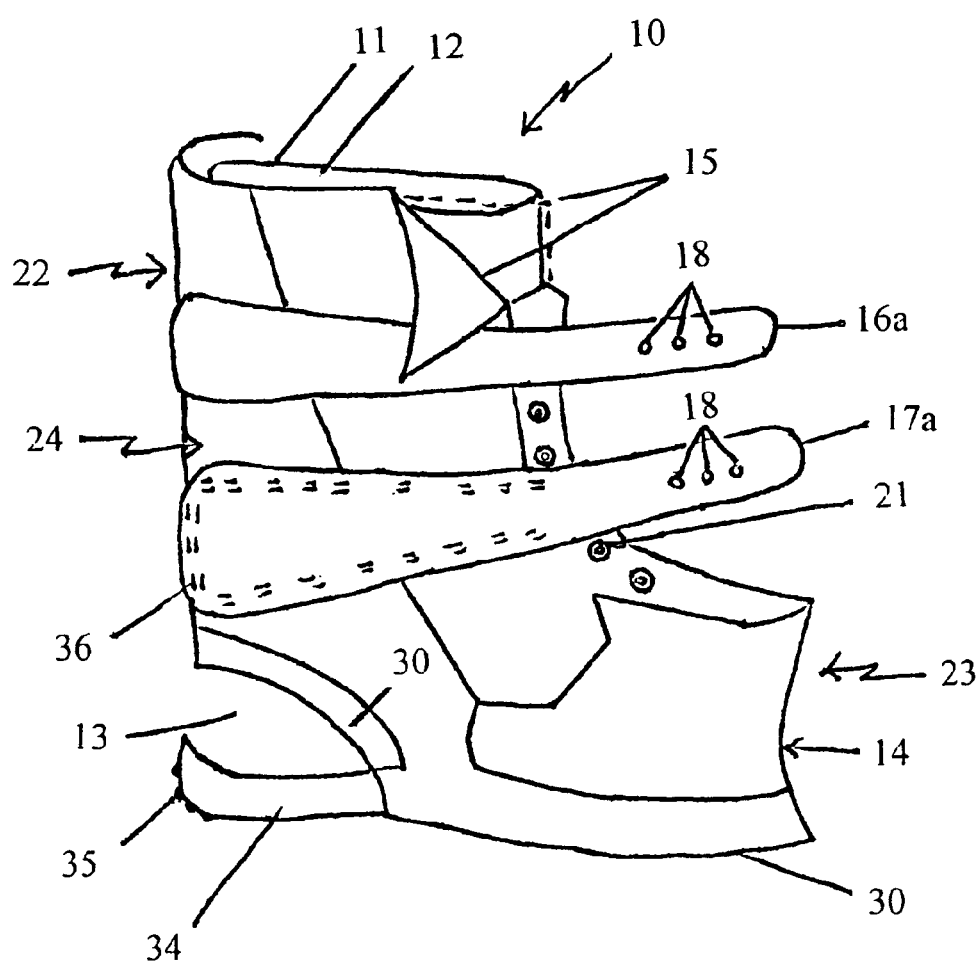
FIG. 1 is an elevational side view of a brace according to the present invention.

In the following description, like reference characters designate like or corresponding parts throughout the several views. Also, in the following description, it is to be understood that such terms as "front," "back," "within," and the like are words of convenience and are not to be construed as limiting terms. Referring in more detail to the drawings, the invention will now be described.

Turning first to FIG. 1, a foot and ankle brace 10 according to the present invention is constructed to enhance comfort, stabilization and the ease of use during the process of rehabilitation and after. The foot and ankle brace 10 is shown in FIGS. 1 through 10 at various angles and positions.

The foot and ankle brace 10 has complete support throughout, beginning with an inner support layer 11, which is shown in FIG. 1. This inner support layer 11 is preferably made from a spandex stretchable support or a thick nylon support. This portion is closely fitted around the ankle and foot, allowing the area to breathe while keeping the muscles and ligaments warm and allowing the blood to flow through blood vessels in the foot and ankle area. The brace 10 includes an upper opening 12, a rear heel opening 13, and a front toe opening 14, as depicted in FIG. 1. The individual user slides his or her foot through the opening in the top of the brace; the user's heel and toes are exposed.

Figure 3:
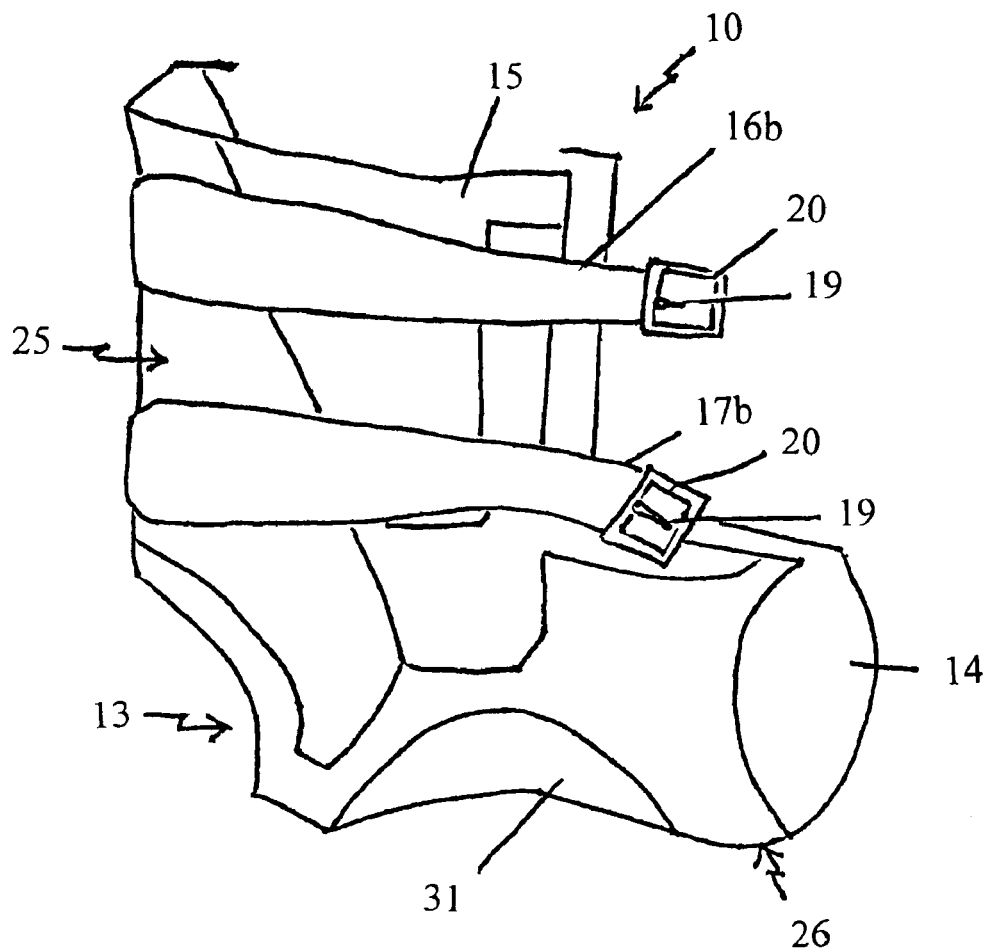
FIG. 3 is a side perspective view of a brace according to the present invention.

Referring to FIGS. 1 and 3, an outer portion 15 of the brace is strong but flexible, and is preferably made of a neoprene or prepared canvas. The brace 10 has at least two layers, including the outer portion 15, which holds the inner structure of splints along with urethane cushioning between the two. Preferably, the inner layer is adhered (e.g., by gluing or other adhesive) to the outer layer portion, so that it is not an independent structure, with a substantial amount of cushioning between the outer layer portion and the inner layer. The relatively rigid splints are preferably adhered to the inner layer, with cushioning preferably overlying the splints. The inner brace support layer 11 is preferably heavily stitched at the upper opening 12, the opening for the toes 14, and down the back of the brace. When the inner brace support layer 11 is easily slipped on, the outer brace portion 15 is would be properly in place at the same time.

Thus, the brace 10 is comprised of at least two layers: an innermost support layer 11, which is comprised of an elasticized, close-fitting material; and an outer portion 15 comprised of at least one layer of a substantially rigid, yet flexible, protective material.

Figure 2:
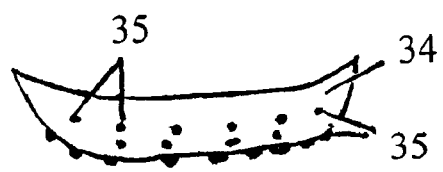
FIG. 2 is a rear elevational view of a calcanus heel portion of a brace according to FIG. 1.

Once the brace is placed in position over the ankle, it is held on by both laces (not shown) and support straps that give the brace extra support when tightened. An upper strap 16 and a lower strap 17 give the brace extra stability, which is provided in two major areas that will keep the ankle in place. One is positioned high, wrapping around the tibia and fibula area between the ankle and the calf. Strap 17 is slightly wider in the back and narrows as it gets closer to the end to the buckle and duplicates its self on the other side of the brace. The lower strap 17 is positioned across the joint of the ankle, supporting the superior and inferior extensor retinacula. As shown in FIGS. 1 and 2, a first strap member 16a, 17a of each of the straps have a number of holes 18 for receiving an insertable member 19 of a buckle 20 on a corresponding strap member 16b, 17b of the strap.

As shown in FIGS. 1 and 3, along with the straps are laces that give a tighter fit for support. A series of circular openings 21 along a front midline of the brace receive the laces (not shown). The laces provide strength and secure the splints in place. Once the laces are tightened, all of the splints will be locked into position to give the proper support.

Figure 6:
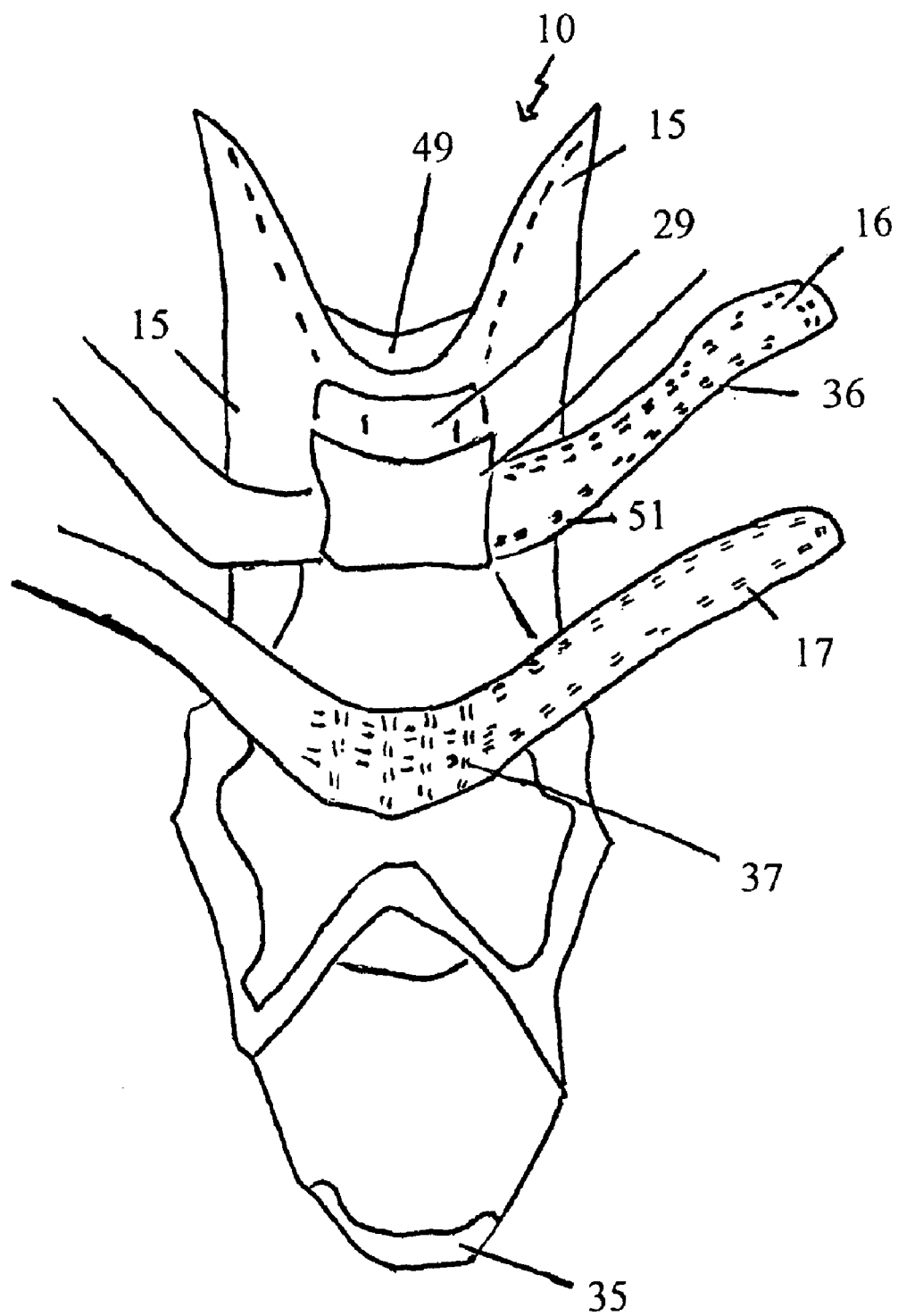
FIG. 6 is a rear perspective view of a brace according to the present invention.

Turning to FIG. 6, the brace 10 further comprises at least five splints, each adjacent to the outer portion 15. The splints are preferably adhered to the inside surface of the outer portion 15, as by gluing. Alternatively, the splints may be incorporated into the outer portion 15, as by sandwiching the splints between several layers of outer portion material. For purposes of discussion, the outer portion 15 can be divided into an upper portion 22 above the wearer's ankle area, a bottom portion 23 below the wearer's ankle area, an outside section 24 of the brace along the outside of the wearer's foot, as shown in FIG. 1, an inside section 25 of the brace along the inside of the wearer's foot, as shown in FIG. 3, and a soft or hard sole 26 under the brace connecting the bottom edges of the outside 24 and inside 25 sections of the brace. For purposes of illustration, the brace 10 is shown in a flattened position in FIG. 6, with the sole 26 extending downward from the inside section 25.

Continuing to refer to FIG. 6, a first, generally L-shaped splint 27 is positioned with its generally vertical longitudinal axis over the area of the wearer's fibula, although the brace does not extend up over the entire lower leg of the wearer. The brace ordinarily extends up past the ankle but well below the knee. The first, fibula splint 27 extends along the outside 24 of the brace 10, with the shorter leg 27b of its L-shape extending in a generally horizontal direction along the bottom portion 23 of the brace.

On the opposite, inside section 25 of the brace, a matching, second, generally L-shaped splint 28 has its longitudinal axis over the wearer's tibia. This second, tibia splint 28 extends along the inside of the brace 10, with its shorter leg 28b also extending in a generally horizontal direction along the bottom portion 23 of the brace.

The L-shaped tibia and fibula splints on both sides of the foot and ankle 27, 28 provide support and protection from inversion and eversion of the ankle. These tibia and fibula splints 27, 28 extend in a generally vertical direction alongside a bottom part of the wearer's tibia and fibula.

A third one 29 of the splints extends in a generally vertical direction in the rear of the brace 10 over the wearer's Achilles tendon, also called the calcaneal tendon. The rear of the brace is between the outside side 24 of the brace and the inside side 25 of the brace. The inside side 25 of the brace is generally opposite the outside side 24 of the brace. This Achilles tendon splint 29 is preferably straight, with a forked lower end for a more comfortable fit over the top of the wearer's heel. The cut-out heel opening 13 in the rear of the brace allows the wearer's heel to protrude through for comfort and to facilitate walking.

Figure 7:
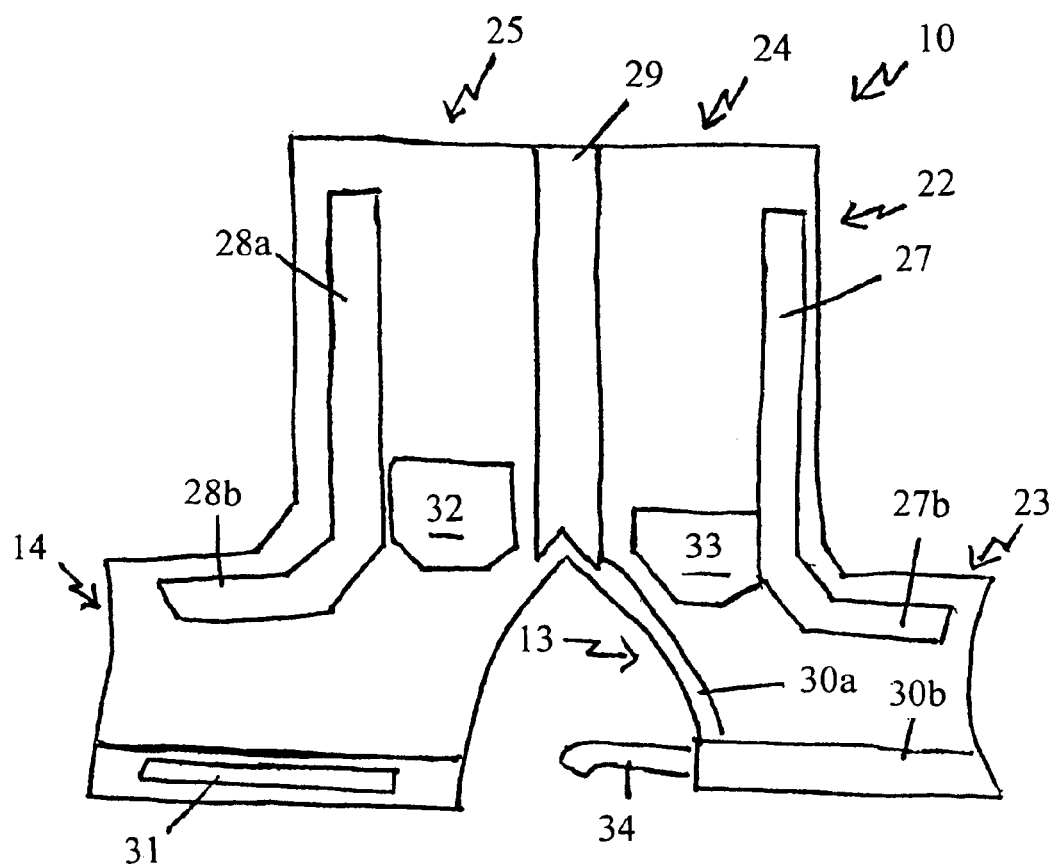
FIG. 7 is an elevational view of an inside of a flattened brace according to the present invention.

As is also shown in FIG. 7, a fourth one 30 of the splints extends in a generally horizontal direction along an outside of the brace 10. The generally V-shaped fourth, fifth metatarsal splint extends over the wearer's fifth metatarsal, which extends along the outer edge of the foot. This fifth metatarsal splint 30 ends at the lower, forked end of the third, Achilles tendon splint, with the rear branch 30a of its "V" shape extending along one side of the rear, heel opening 13. An opposite end of the fifth metatarsal splint 30 ends at the front, toe opening 14 of the brace, with a front branch 30b of its "V" shape bordering the bottom edge of the outside section 24 of the brace. The wearer's phalanges, or toes, protrude through the front, toe opening 14, although an alternate embodiment of the brace has a closed-in toe.

The fifth metatarsal splint 30 extends from the Achilles tendon splint. This splint assists the splints on the outside leg when making quick lateral and bilateral movements. The fifth metatarsal splint 30 is believed to provide stability, decrease the chances of eversion of the ankle, and protect the tendon of peroneus longus and peroneus tartius. Along the inside of the fifth metatarsal splint 30 is a considerable amount of urethane foam for extra comfort and support. The fifth metatarsal splint preferably shapes and wraps around the side of the foot and about a half inch under the foot.

Continuing with FIGS. 3 and 7, a fifth one of the splints in the foot and ankle brace 10 is an arch support splint 31. The arch support splint supports the arch, which is on the bottom of the foot to the inside of the center of the foot. Like the natural arch of the foot, the arch support splint 31 arches up at the approximate mid-center of the bottom of a brace 10 on the inside side. Since the wearer will be walking around on the brace 10, it is important that the arch is supported, particularly where the wearer has a weak or fallen arch.

Continuing with FIG. 7, a sixth one of the splints in the foot and ankle brace 10 is a medial malleolus splint 32, which can be seen on the inside of the brace. The slightly concave medial malleolus splint 32 protects the small "ankle bone" protrusion, or medial malleolus, on the inside of the wearer's ankle.

Continuing with FIG. 7, a seventh one of the splints in the foot and ankle brace 10 is a lateral malleolus splint 33, which protects the small "ankle bone" protrusion, or lateral malleolus, on the outside of the wearer's ankle. The slightly concave lateral malleolus splint 33 cups the lateral malleolus.

These padded medial and lateral malleolus splints fit around the joint of the ankle on both sides at the lateral and medial malleolus The medial and lateral malleolus splint 32, 33 may be connected to the longer legs of the tibia and fibula splints 28, 27, respectively, for more stationary support. Underneath each of these splints is a layer of padding with urethane foam. These give protection to the flexor renticulum while providing comfort and a moderate level of compression to the ankle area.

Referring again to FIG. 1, foot and ankle brace 10 further includes a calcaneal support 34, which provides stationary support to the calcanus or the heel of the foot. This structure helps to control the foot and ankle areas while imparting sheer comfort to the wearer with a tender ankle. The anterior end of the calcaneal support 34 is connected to the fifth metatarsal splint 30 at the juncture of the two legs 30a, 30b, and protrudes through the two layers of the outside portion. The calcaneal support 34 is preferably made of a solid secure material such as plastic or fiberglass, that protrudes from the rest of the brace. It is slanted at the bottom tip for easy access to the shoe, on those occasions when the brace will be worn with a conventional shoe. Once in the shoe, the back of the heel and bottom of the wearer's foot in the brace will be secure because of the support provided by the calcaneal support 34. The calcaneal support 34 wraps slightly under the foot and around the back of the heel.

As shown in FIGS. 1 and 2, the calcaneal support 34 includes stippling 35 along its back and bottom. The stippling 35 is also preferably present on the outside layer of the brace under the foot to help prevent the foot from slipping. There is also stippling 35 positioned underneath the brace at the location of the wearer's first metatarsal at the joint. The stippling is placed in these particular areas to give stationary support to the areas of the brace that support a majority of a person's weight when the person is presenting the proper foot position. Despite so many different movements, the ankle will remain stationary without any sliding within the shoe.

As shown in FIGS. 1 and 6, stitching 36 is provided on the straps 16, 17. The thicker portion of the strap 17a, which is attached to the outside portion of the brace, has stitching to make it stationary. As the stitching goes down the strap toward the tip, the stitching will only go through the two layers of the strap itself.

As shown in FIG. 6, the foot and ankle brace 10 has heavy stitching in the back of both straps, preferably with double lines of stitching horizontally and vertically. The vertical stitching is preferably double stitching split into three different segments 37. The heavy stitching 36, 37 provides strength and durability to the straps when they are locked in a secure position.

As depicted in FIG. 6, the Achilles tendon splint 29, which helps protect the Achilles tendon, shapes the back portion of the ankle. It fits securely behind the ankle joint for a secure comfortable fit.

Figure 5:
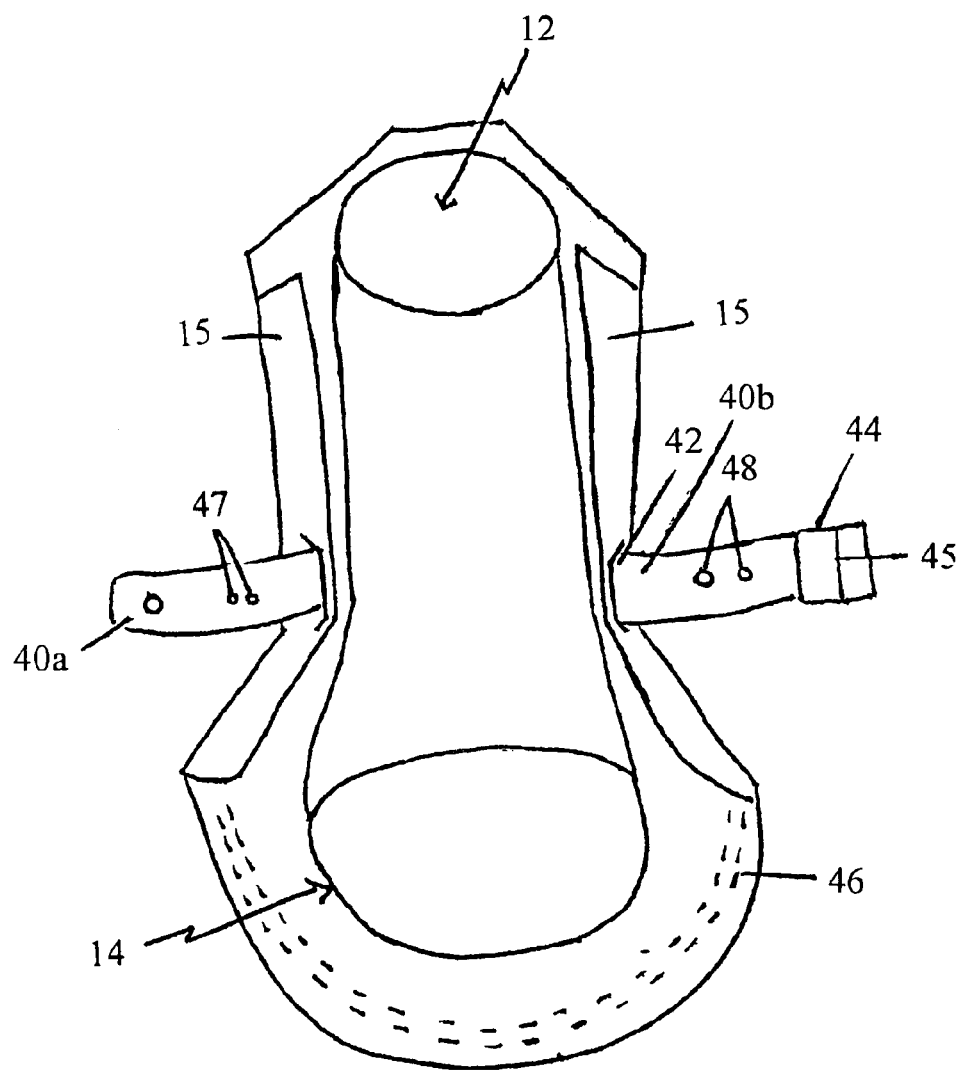
FIG. 5 is a front perspective view of an open brace according to the present invention.

Referring to FIGS. 1, 3 and 5, the second strap members 16b, 17b of the straps receive and lock the first strap members with the adjustable comfort destinations. This second strap member 16b, 17b is slightly shorter than the first strap member 16a, 17a. This allows the upper and lower first strap members 16a, 17a cross the front of the ankle and connect to the strap buckles 20 on the second strap members 16b, 17b.

As shown in FIGS. 3 and 7, the arch support splint 31 gives the ankle stability and holds the ankle in place. The weight of the individual will rest on the foot in the proper position, therefore keeping the ankle stabilized. This particular arch support will play a major role in helping to prevent inversion of the ankle. The inside of the brace 10 is preferably lined with urethane foam or the like to provide soothing comfort. The splint gives the wearer protection along the flexor longus, and peltoid of the internal lateral ligament.

As shown in FIG. 7, the lateral malleolous splint 33 cups the ankle joint, supporting the L-shaped first, fibula splint and arch support splint 31 to protect against eversion of the ankle. The lateral malleolous splint 33 is preferably made of plastic with a layer of urethane foam underneath for both support and comfort.

Figure 4:
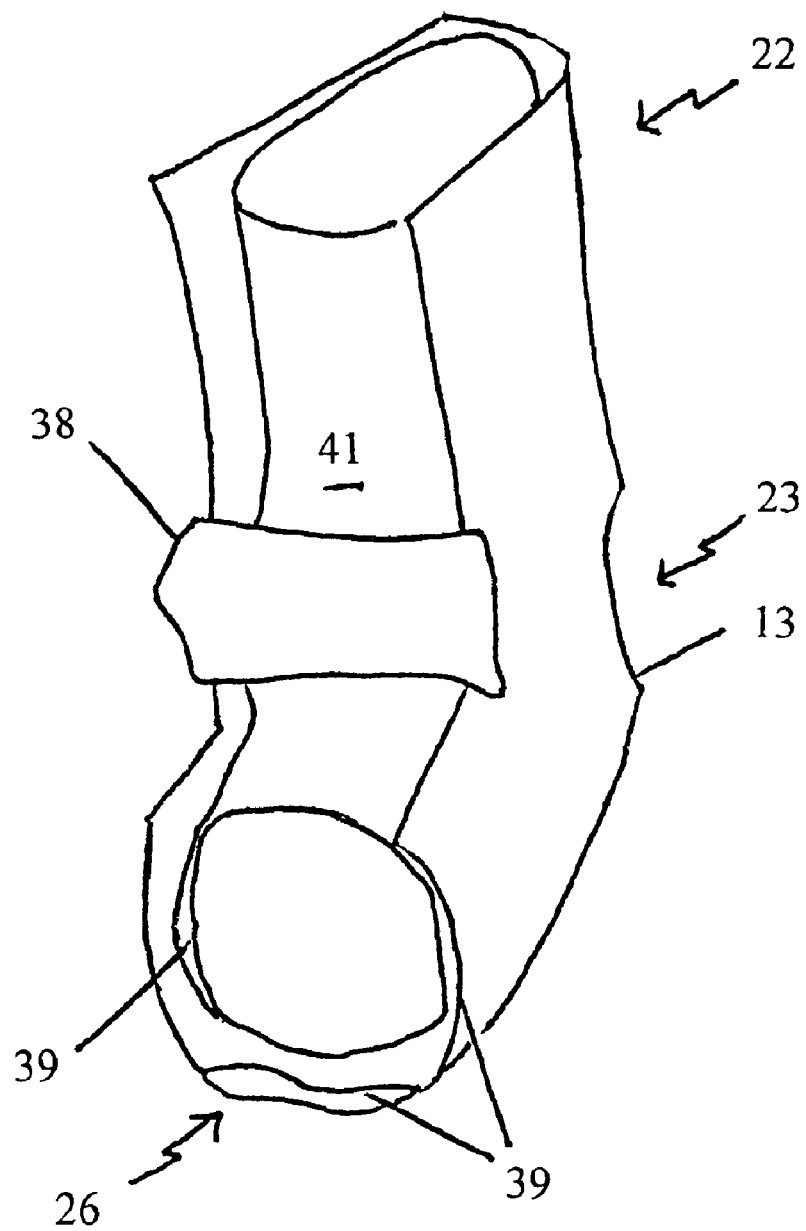
FIG. 4 is a front perspective view of a brace according to the present invention.

Ankle brace 10 also provides a padded tongue 38, as illustrated in FIG. 4, which extends across the top of the foot for providing comfort to the wearer once all support devices are locked and secured in place. The tongue 38 is preferably made of the same material as the outer portion of the brace. It is 2-ply and is stuffed with urethane foam. The rear heel opening 13 that the wearer's heel will protrude through is also seen in FIG. 4.

The foot and ankle brace is preferably provided with padding or cushioning throughout the brace, particularly between the splints and the inner layer of the brace. As shown in FIG. 4, padding 39 extends along the bottom of the brace, and elsewhere in the brace between the inner and outer layers, to give the wearer comfort while moving around in the brace. The padding 39, or cushioning, gives the wearer a feeling of elevation and helps relieve some stress off the lower shin when the wearer is moving about on hard surfaces.

Figure 8:
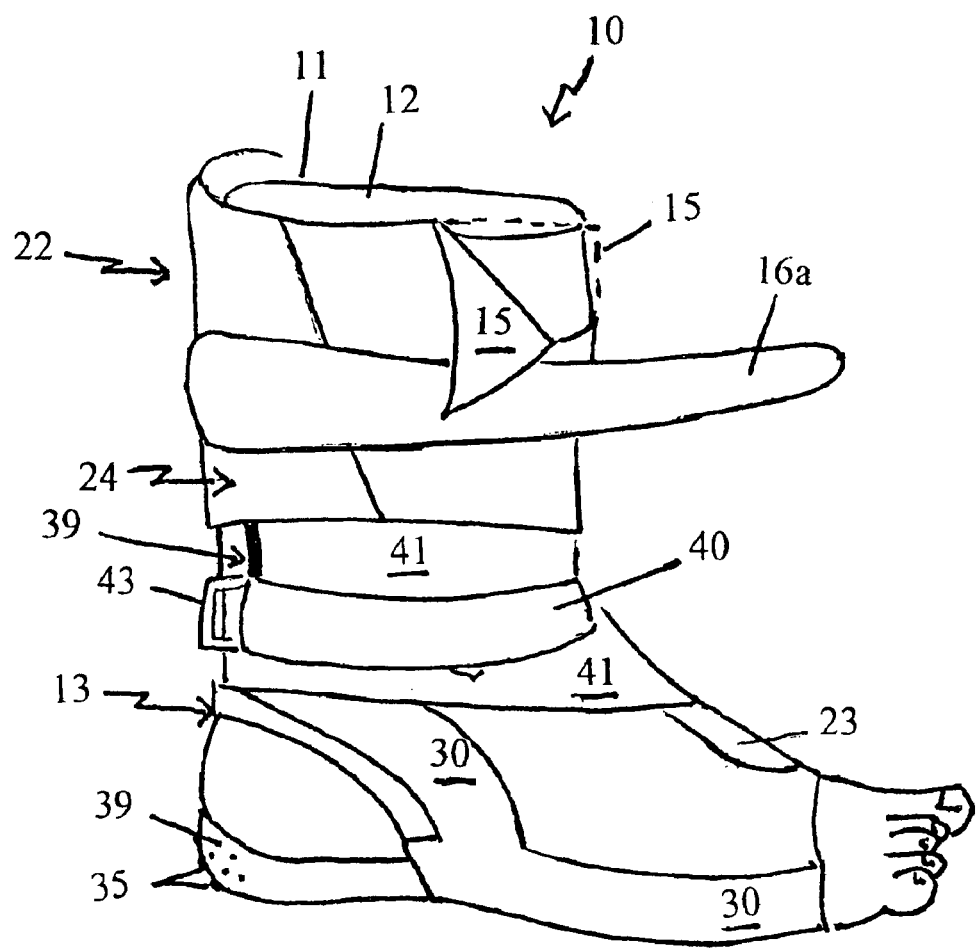
FIG. 8 is a side perspective view of a brace according to the present invention, shown in use on a foot.
Figure 9:
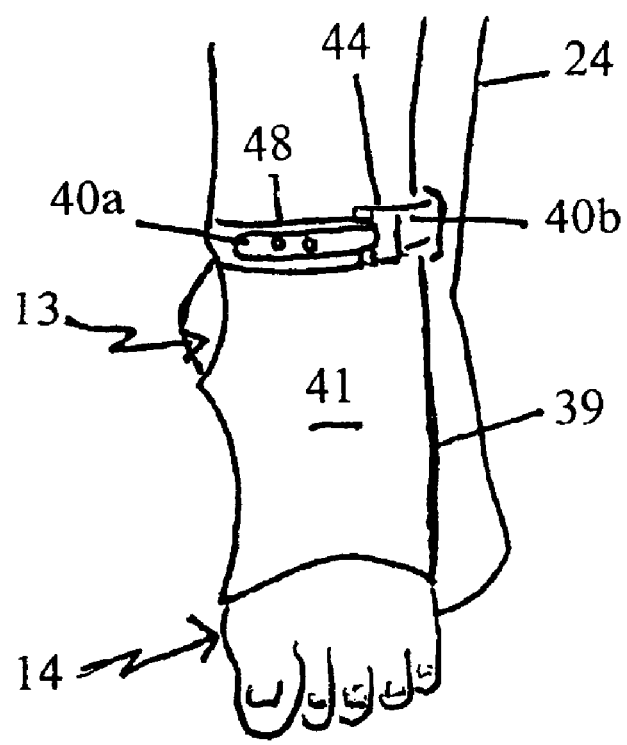
FIG. 9 is a front perspective view of a portion of a brace according to the present invention, shown in use on a wearer's foot.

Referring to FIGS. 5, 8 and 9, one embodiment of the foot and ankle brace 10 has an elasticized band 40 that protrudes through the outside portion of the brace at its rear (as seen in FIGS. 5 and 8). This stretchable band is adapted for covering and protecting the superior and inferior extensors. The resulting compression around the ankle will remove stress from the tendon and surrounding tissues, particularly when the wearer is involved in physical activity. For purposes of illustrating the band 40 underneath, the outer layers of the brace are shown cut away in FIG. 8. The band 40 is fastenable around a soft, flexible inner sock portion 41 of the brace 10. The sock portion is preferably substantially independent of the brace, so that is comfortable, and only connected to the inner support layer 11 at the top of the brace at the upper opening 12, so that it is less likely to creep down around the wearer's ankle as the day progresses. In FIG. 5, for purposes of illustration, the front of the brace is shown splayed open to reveal the sock portion and an open band 40. To use the brace 10, the wearer inserts the injured foot into the upper opening 12 of the brace and down through the sock portion 41, until the wearer's toes protrude through the front toe opening 14 and his or her heel rests in the rear heel opening 13. A portion 43 of the elasticized band passes through slots 42 in the outer layer portion of the brace, as shown in FIGS. 5 and 8, so that the band 40 is fastened through part of the brace and does not press heavily on the ankle. Although this band 40 around the sock portion 41 provides extra support, it is left to the individual to determine if they want to use it. An individual can put on the brace after twisting their ankle, and apply compression to reduce swelling by fastening the elasticized band 40 around the front of the sock portion, if desired. This particular band 40 goes over the tongue 38 of the brace. The cushioning of the tongue 38 provides comfort as compression from the band 40 is applied.

The band 40 is preferably in two segments, a first band segment 40a, and a second band segment 40b. At the end of the second band segment 40b, a latch 44 is attached that will allow the band 40 to be tightened to a desired position before locking. A center bar 45 across the latch 44 allows the band segments 40a, 40b to be tightened; it will provide the resistance when the band is being pulled to the desired place. FIG. 5 displays the double stitching 46 that will go along the front outside layer of the ankle brace 10.

As shown in FIGS. 5 and 9, an end portion of the first band segment 40a is passed around the center latch bar 45. Once the end of the first band segment is fastened around the latch bar 45, one or more pins 47 attached to the inside of the first band segment 40a are fastened down into corresponding holes 48 in the end portion of the first band segment in the outside of the second band segment 40b. Several pins 47 and corresponding holes 48 offer a choice of settings for the band segments, so that the wearer can choose a comfortable degree of compression on the ankle. The pins 47 and latch 44 are preferably made of plastic.

As shown in FIG. 6, in the back area between the inner and outer portion of the brace 10, urethane foam 49 is placed to offer extra comfort and support. A cut-out in FIG. 6 shows the Achilles tendon splint 29, as shown from the rear. The Achilles tendon splint 29 is preferably bent along its longitudinal midline bends so that it curves around the outside of the wearer's ankle and lower leg for more adequate support.

As seen in FIG. 6, lines of double stitching 36 extend along the edge of the straps 16, 17 toward the front of the brace 10. Stitch lines 51 along the rear midline hold the strap to the brace giving support along both straps extending past the Achilles tendon splint. The stitching on the back of the straps is preferably doubled and in four different rows. On both straps 16, 17, the stitching 36 is heavy for durability and strength. As shown in FIG. 6, the brace is padded inside with urethane foam for comfort when walking, running, etc.

Figure 10:
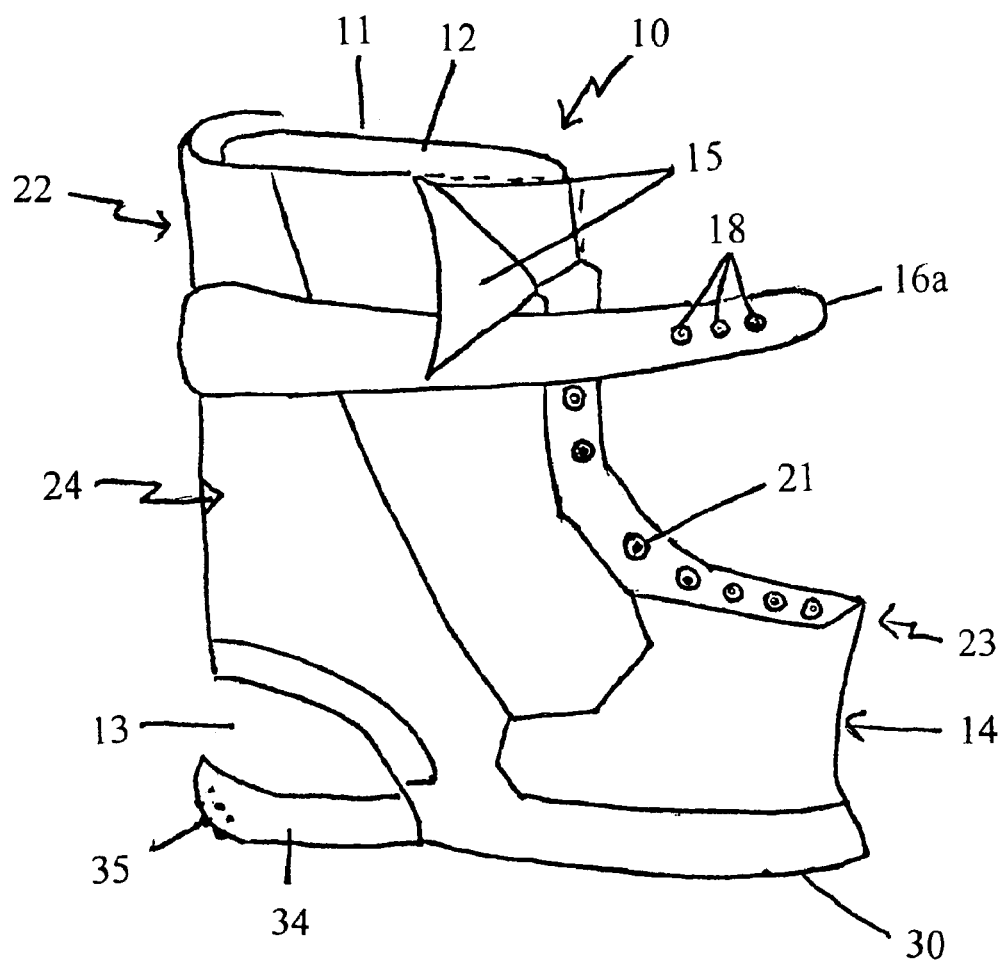
FIG. 10 is an elevational side view of a brace according to the present invention, showing a single strap embodiment.

Lastly, FIG. 10 shows an embodiment of the present invention having a single strap 16.

The splints and the outer (or inner) portion of the present brace 10 are preferably not unitarily injection molded, with or without the straps (in the injection mold), and do not form a single unitary support. The splints of the present invention are preferably not made of strips of wood or metallic plates. Since the present invention includes an arch support splint, there is no need for any strap extending under the arch of the wearer's foot. The present brace 10 extends around and supports the wearer's entire ankle and lower leg.

From the foregoing it can be realized that the described device of the present invention may be easily and conveniently utilized as a foot and ankle brace. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Brief List of Reference Numbers Used in the Drawings 10 foot and ankle brace
11 inner support layer
12 upper opening
13 rear heel opening
14 front toe opening
15 outer portion
16 upper strap
17 lower strap
18 strap holes
19 insertable member
20 strap buckle
21 lace openings
22 uppper portion
23 bottom portion
24 outside of brace
25 inside of brace
26 sole of brace
27 first, fibula splint
28 second, tibia splint
29 third, Achilles tendon splint
30 fourth, fifth metatarsal splint
31 fifth, arch support splint
32 sixth, medial malleolus splint
33 seventh, lateral malleolus splint
34 calcaneal support

What is claimed is:

1. A brace for supporting the ankle or foot of a wearer, the brace comprising:
   (a) at least two layers, an inner one of the at least two layers being comprised of an elasticized, close-fitting material, an outer portion of the layers being comprised of a supportive, yet flexible, protective material; and
   (b) at least four splints, each attached to the outer layer portion, with a first, generally L-shaped one of the at least four splints having a longitudinal axis leg portion over the wearer's fibula, the first, fibula splint extending along an outside side of the brace; a second, generally L-shaped splint having a longitudinal axis leg portion over the wearer's tibia, the second, tibia splint extending along an inside side of the brace, the inside side of the brace being opposite the outside side of the brace; a third, Achilles tendon splint extending in a generally vertical direction at a rear of the brace over the wearer's Achilles tendon, the rear of the brace being between the inside side and the outside side of the brace; and a fourth, fifth metatarsal splint extending from the Achilles tendon splint in a generally horizontal direction along an outside of the brace.

2. A brace according to claim 1, further comprising a fifth, arch support splint on a bottom of the brace between the outer layer portion and the inner layer of the brace for supporting the wearer's arch.

3. A brace according to claim 1, wherein the splints and the outer or inner portions of the brace are not unitarily injection molded, and do not form a single unitary support.

4. A brace according to claim 3, further comprising at least one first strap, which is extendible around at least a majority of the circumference of the outer portion.

5. A brace according to claim 4, further comprising a sixth, generally cup-shaped medial malleolus splint inside the brace in an inside ankle area of the brace.

6. A brace according to claim 5, further comprising a second strap, which is extendible around the circumference of the outer portion below the first strap, the first and second straps each being comprised of two strap members.

7. A brace according to claim 3, further comprising a seventh, generally cup-shaped lateral malleolus splint between the outer layer portion and the inner layer of the brace on the outside side of the brace in the ankle area.

8. A brace according to claim 7, further comprising a cut-out heel opening.

9. A brace according to claim 1, wherein a shorter leg portion of each of the generally L-shaped tibia and fibula splints, the end of which is connected to the longer, longitudinal axis leg portion of the tibia or fibula splint, extends in a generally horizontal direction along the bottom portion of the brace.

10. A brace according to claim 9, further comprising a cut-out front toe opening.

11. A brace according to claim 1, further comprising a flexible innermost sock portion, which is closely fitable around an ankle of the wearer, a portion of the sock portion being connected to an inner layer of the brace.

12. A brace according to claim 11, further comprising an elasticized band fastenable around the sock portion, a portion of the elasticized band passing through slots in the outer layer portion of the brace.

13. A brace according to claim 12, wherein the band is comprised of two corresponding band segments fastenable by a fastening mechanism.

14. A brace according to claim 13, wherein the fastening mechanism is a latch attached to an end of a second one of the band segments, the latch having a center bar around which an end portion of a first one of the band segments is passed.

15. A brace according to claim 10, wherein the inner layer is adhered to the outer layer portion, with a substantial amount of cushioning between the outer layer portion and the inner layer.

16. A brace according to claim 6, wherein the splints are adhered to the innermost layer of the outer portion, with cushioning overlying the splints and the inner layer being adhered to the splints and the inside face of the outer layer portion.

17. A brace according to claim 16, wherein one of the strap members of each of the straps has a plurality of holes for receiving an insertable member of a buckle attached to a corresponding strap member of the strap.

* * * * *